United States Patent
Mullis et al.

[11] Patent Number: 5,967,977
[45] Date of Patent: Oct. 19, 1999

[54] TRANSESOPHAGEAL MEDICAL LEAD

[75] Inventors: Deniz Ayaz Mullis, Baltimore, Md.;
Kristi M. Legatt, Minnetonka, Minn.

[73] Assignee: Medtronic, Inc., Minneapolis, Minn.

[21] Appl. No.: 08/943,850

[22] Filed: Oct. 3, 1997

[51] Int. Cl.⁶ .................................................. A61B 5/04
[52] U.S. Cl. ........................ 600/380; 600/373; 607/124
[58] Field of Search .................................. 600/374, 375, 600/380, 381, 393; 607/122, 124, 126

[56] References Cited

U.S. PATENT DOCUMENTS

| | | |
|---|---|---|
| 3,517,128 | 6/1970 | Hines . |
| 4,304,240 | 12/1981 | Perlin . |
| 4,576,162 | 3/1986 | McCorkle . |
| 4,640,298 | 2/1987 | Pless et al. . |
| 4,699,147 | 10/1987 | Chilson et al. . |
| 4,706,688 | 11/1987 | Don Michael et al. . |
| 4,722,347 | 2/1988 | Abrams et al. . |
| 4,817,611 | 4/1989 | Arzbaecher et al. . |
| 4,883,070 | 11/1989 | Hanson . |
| 4,920,979 | 5/1990 | Bullara . |
| 4,930,521 | 6/1990 | Metzger et al. . |
| 4,946,457 | 8/1990 | Elliott . |
| 5,010,894 | 4/1991 | Edhag . |
| 5,117,828 | 6/1992 | Metzger et al. . |
| 5,154,387 | 10/1992 | Trailer . |
| 5,170,803 | 12/1992 | Hewson et al. . |
| 5,239,999 | 8/1993 | Imran . |
| 5,263,493 | 11/1993 | Avitall . |
| 5,370,679 | 12/1994 | Atlee, III . |
| 5,379,765 | 1/1995 | Kajiwara et al. . |
| 5,387,232 | 2/1995 | Trailer . |
| 5,406,946 | 4/1995 | Imran . |
| 5,417,713 | 5/1995 | Cohen . |
| 5,431,696 | 7/1995 | Atlee, III . |
| 5,449,381 | 9/1995 | Imran . |
| 5,471,982 | 12/1995 | Edwards et al. . |
| 5,782,239 | 7/1998 | Webster, Jr. . |

OTHER PUBLICATIONS

"Trans–Esophageal Pacing," *Pace* 6(1):674–679, Jul.–Aug. 1983.

"Atrial Pacing Thresholds Measured in Anethetized Patients with the Use of an Esophageal Stethoscope Modified for Pacing," *Anesthesiology*, vol. 74, No. 5, 854–859; May 1991.

"Transesophageal Atrial Pacing—Stimulation and Discomfort Thresholds: The Role of Electrode Configuration and Pulse Width" *Pace* vol. 14; pp. 1359–1366, Sep. 1991.

"Esophageal Balloon Electrode Catheter for Transthoracic Recording of His–Bundle Potential with Transesophageal Atrial Pacing" *Pace* vol. 17; 2125–2128, Nov. 1994, Part II.

*Primary Examiner*—Linda C. M. Dvorak
*Assistant Examiner*—Roy Gibson
*Attorney, Agent, or Firm*—Thomas F. Woods; Harold R. Patton

[57] ABSTRACT

A mechanically expandable esophageal medical lead has an elongated flexible body which carries at a distal end thereof one or more electrically conducting members. The conducting members are moveable laterally with respect to the body portion of the medical lead by means of a mechanical structure contained therein. The degree and extent of mechanical movement can be controlled through manipulation of a pull wire axial movement mechanism.

23 Claims, 11 Drawing Sheets

TRANSESOPHAGEAL MEDICAL LEAD

FIELD OF THE INVENTION

The present invention relates to cardiac monitoring and sensing probes. More particularly, the present invention relates to transesophageal medical leads for cardiac pacing, defibrillating and monitoring functions.

BACKGROUND OF THE INVENTION

U.S. Pat. No. 4,817,611 to Arzbaecher et al. entitled "Esophageal Electrocardiography Electrodes" discloses a bipolar electrode usable for esophageal cardiac pacing or cardiac monitoring. The bipolar electrode of the Arzbaecher et al. patent has a molded plastic body which lockingly carries first and second spaced-apart conducting bands.

Other types of esophageal insertable devices are known in the art. Some of these have regions or balloons which may be inflated to block portions of the esophagus or for positioning a unit in the esophagus. Those devices typically require the introduction of air, saline or other fluid for inflation and distention.

Few known devices provide a simple mechanically expandable electrode carrying member which, as a result of expansion and distention, provide improved contact between the interior surface of the esophagus and the conducting elements of the electrode and that also may be reoriented within the esophagus after emplacement to position the stimulating or monitoring electrodes disposed on the distal end thereof in closer proximity to cardiac tissue. Thus, there continues to exist a need for esophageal medical leads that may be easily expanded upon insertion and subsequently repositioned, but that are also cost effective to manufacture.

Disclosures relating to transesophageal and other devices include the patents and other references listed below in Table 1.

TABLE 1

Prior Art Publications

U.S. Patents

| | | | |
|---|---|---|---|
| 3,517,128 | 6/1970 | Hines | 606/198 |
| 4,304,240 | 12/1981 | Perlin | 128/642 |
| 4,576,162 | 3/1986 | McCorkle | 128/419P |
| 4,640,298 | 2/1987 | Pless et al | 128/784 |
| 4,699,147 | 10/1987 | Chilson et al. | 128/642 |
| 4,706,688 | 11/1987 | Don Michael et al. | 128/785 |
| 4,722,347 | 2/1988 | Abrams et al. | 128/663 |
| 4,817,611 | 4/1989 | Arzbaecher et al. | 128/642 |
| 4,883,070 | 11/1989 | Hanson | 128/419P |
| 4,920,979 | 5/1990 | Bullara | 128/784 |
| 4,930,521 | 6/1990 | Metzger et al. | 128/786 |
| 4,946,457 | 8/1990 | Elliott et al. | 606/1 |
| 5,010,894 | 4/1991 | Edhag et al. | 128/785 |
| 5,117,828 | 6/1992 | Metzger et al. | 128/642 |
| 5,154,387 | 10/1993 | Trailer | 128/784 |
| 5,170,803 | 12/1992 | Hewson et al. | 128/786 |
| 5,263,493 | 11/1993 | Avitall | 7/1992 |
| 5,370,679 | 12/1994 | Atlee, III | 607/124 |
| 5,379,765 | 1/1995 | Kajiwara et al. | 128/642 |
| 5,406,946 | 4/1995 | Imran | 128/642 |
| 5,417,713 | 2/1993 | Cohen | 607/4 |
| 5,431,696 | 7/1995 | Atlee, III | 607/124 |
| 5,449,381 | 9/1995 | Imran | 607/122 |

Foreign Patents

| | | | |
|---|---|---|---|
| 0009732 | 4/1980 | European Patent Org. | 128/786 |

TABLE 1-continued

Prior Art Publications

Technical Papers

"Trans-Esopageal Pacing," Andersen et al., PACE, Vol. 6, pp. 674–679, July, 1983.
"Atrial Pacing Thresholds Measured in Anesthetized Patients with the Use of an Esophageal Stethoscope Modified for Pacing," Pattison et al., Anesthesiology, Vol. 74, pp. 854–858, May, 1991.
"Transesophageal Atrial Pacing -- Stimulation and Discomfort Thresholds: The Role of Electrode Configuration and Pulse Width," Res et al., PACE, Vol. 14, pp. 1359–1366, September, 1991.
"Esophageal Balloon Electrode Catheter for Transthoracic Recording of His-Bundle Potential with Transesophageal Atrial Pacing," Heinke et al., PACE, vol. 17, pp. 2125–2128, November, 1994.

As those skilled in the art will appreciate upon reading the Summary of the Invention, Detailed Description of the Preferred Embodiments and Claims set forth below, at least some of the devices and methods disclosed in the patents of Table 1 may be modified advantageously by using the teachings of the present invention.

SUMMARY OF THE INVENTION

The present invention has certain objects. That is, the present invention provides solutions to at least some of the problems existing in the prior art respecting transesophageal pacing, defibrillating and monitoring devices. At least some aspects of conventional devices may be characterized as:

(a) requiring high pacing thresholds;
(b) causing patient discomfort owing to high pacing thresholds;
(c) not permitting transfer of a substantial or significant amount of torque or rotational movement from the proximal end of the lead to the distal end of the lead;
(d) having poor sensing or monitoring capabilities;
(e) not being insertable through the nares passageways of a patient at all, or at least without causing great discomfort to the patient;
(f) requiring the use of a balloon which may occlude the esophagus of a patient;
(g) not being removable from a patient without damaging the esophagus or the nasal cavity;
(h) being difficult for a physician to manipulate and emplace;
(i) having only one or a fixed number of electrodes available for pacing, defibrillating or monitoring;
(j) comprising electrodes having fixed spacing therebetween;
(k) having localized electrodes which may exert excessive pressure on the esophagus of a patient and thereby cause localized tissue trauma;
(l) having exposed pull wires which may damage esophageal tissue, and
(m) having distention members which, as a result of their occluding the esophagus during stimulation or monitoring, may cause rupture of the esophagus should patients regurgitate fluid or other matter when the distention members are in an expanded state.

The present invention provides solutions to at least some of the problems associated with conventional transesophageal pacing, defibrillating and monitoring devices.

At least some embodiments of the present invention provide certain advantages, including, but not limited to, a transesophageal medical lead that:

(a) provides a safer, more comfortable means of pacing a patient;

(b) does not cause tissue trauma;

(c) does not occlude the esophagus;

(d) may be removed from a patient while the distal end of the lead is distended, without damaging the esophagus;

(e) permits the transfer of a substantial or significant amount of torque or rotational movement from the proximal end of the lead to the distal end of the lead;

(f) requires lower pacing thresholds than heretofore attainable;

(g) is insertable through the nares passageway of a patient;

(h) is relatively easy for a physician to manipulate and emplace;

(i) has a selectable number of electrodes available for pacing, defibrillating or monitoring;

(j) has selectable electrode spacing;

(k) has no exposed wires or structures that may damage or cause trauma to esophageal tissue, and (l) may be employed transnasally or transorally.

At least some embodiments of the present invention have certain features, including, but not limited to, a transesophageal medical lead having one or more of the following features:

(a) no, or substantially no, hard angle structures disposed on the distal end of the lead that might otherwise cause tissue damage or trauma;

(b) an expandable or distendable mechanism located near the distal end of the lead;

(c) an expandable or distendable mechanism located near the distal end of the lead that expands symmetrically;

(d) an expandable or distendable mechanism located near the distal end of the lead that does not substantially occlude the esophagus, at least to the extent that swallowing is not impeded substantially or prevented in a subject;

(e) a flexible tip or portion disposed at or near the distal end of the lead, the tip or portion being suitable for insertion through the nares passageway of a patient;

(f) a plurality of electrodes disposed on the expandable or distendable mechanism for pacing, defibrillating or monitoring a patient's heart;

(g) electrodes that may be configured with spatially variable inter-electrode spacing;

(h) a lead body coil that is sufficiently mechanically robust to permit the transfer of a substantial or significant amount of torque or rotational movement from the proximal end of the lead to the distal end of the lead;

(i) a pull wire disposed within the lead body and extending between the proximal and distal ends, which when drawn taut or pushed causes the expandable or distendable mechanism to expand outwardly to engage the sidewalls of the esophagus;

(j) a rotatable mechanism disposed near or at the proximal end of the lead that upon being rotated by a user either distends or closes the expandable or distendable mechanism located near or at the distal end of the lead;

(k) an expandable or distendable mechanism comprising a plurality of extendible, distendable arms, the arms being extendible or retractable by a user through rotation of a handle assembly or the pulling or pushing of a pull wire, (l) an expandable or distendable mechanism having an outside diameter that may be varied continuously through pull wire retraction or other means.

In accordance with the present invention, an expandable or distendable esophageal medical lead is provided which includes a mechanical structure or distention mechanism for expansion and retraction, most preferably symmetrical, of at least one, or more preferably yet a set, of conducting members. The lead includes an elongated flexible lead body having a proximal end and a distal end.

At least one conductive member is attached to, mounted on, forms part of, or is carried on or near the distal end. A plurality of conductive members may, alternatively, be disposed on or near the distal end. The lead includes an expandable mechanical structure or distention mechanism located at or near its distal end for positioning the conductive member or members substantially laterally respecting an imaginary defining the lead body.

In use, the distal end of the medical lead is positioned in the esophagus of a human or other mammalian subject adjacent the posterior surface of the subject's heart. The body of the medical lead is long enough that the proximal end thereof is outside of the body of the subject. The proximal end of the pull wire may then be manipulated manually to mechanically expand the distention mechanism in the esophagus.

Pacing or defibrillating electrical signals may then be applied, via proximal end connectors, and wiring internal to the medical lead, to the electrode members disposed on the distention mechanism. Alternatively, the electrodes disposed on the distention mechanism may be employed to passively monitor cardiac or other biological electrical signals emanating from or generated in the subject. The distention mechanism need not be expanded to its full extent before electrical signals are applied to or monitored by the electrodes.

A significant advantage of the present invention is the degree of control a user may exert over the amount by which the distention mechanism expands in the esophagus through manipulating the pull wire. It is possible to use the medical lead of the present invention with the distention mechanism only partially expanded. Since in some embodiments of the present invention the pull wire may be locked at any intermediate position, the selected degree of expansion of the distention mechanism may be maintained reliably until the end of the procedure.

Numerous other objects, features and advantages of the present invention will become readily apparent from the appended detailed description of the invention, drawings and claims.

DETAILED DESCRIPTION OF THE PREFERRED EMBODIMENTS

While the present invention is susceptible of various embodiments having many different forms, there is shown in the drawing and will be described herein in detail a specific embodiment thereof with the understanding that the present disclosure is an exemplification of the principles of the invention, and is not intended to limit the invention to the specific embodiment illustrated.

As used in the specification and claims hereof, the following terms have the particular meanings and definitions set forth below.

The term "braided" means the interweaving together of individual strands or electrical conductors.

The term "stranded" means the twisting together of individual strands or electrical conductors.

The term "twisted" means the entwining, twisting or twining together of individual strands or electrical wires.

The term "proximal" means that portion of an apparatus, or component or element of an apparatus, which is disposed in closer proximity to the end of the lead that remains outside a patient's body during a lead emplacement procedure than it is to the end of the lead that is inserted first inside the patient's body during the lead emplacement procedure.

The term "distal" means that portion of an apparatus, or component or element of an apparatus, which is disposed in closer proximity to the end of the lead that is inserted first inside a patient's body during a lead emplacement procedure than it is to the end of the lead that remains outside the patient's body during the lead emplacement procedure.

Figure 1:
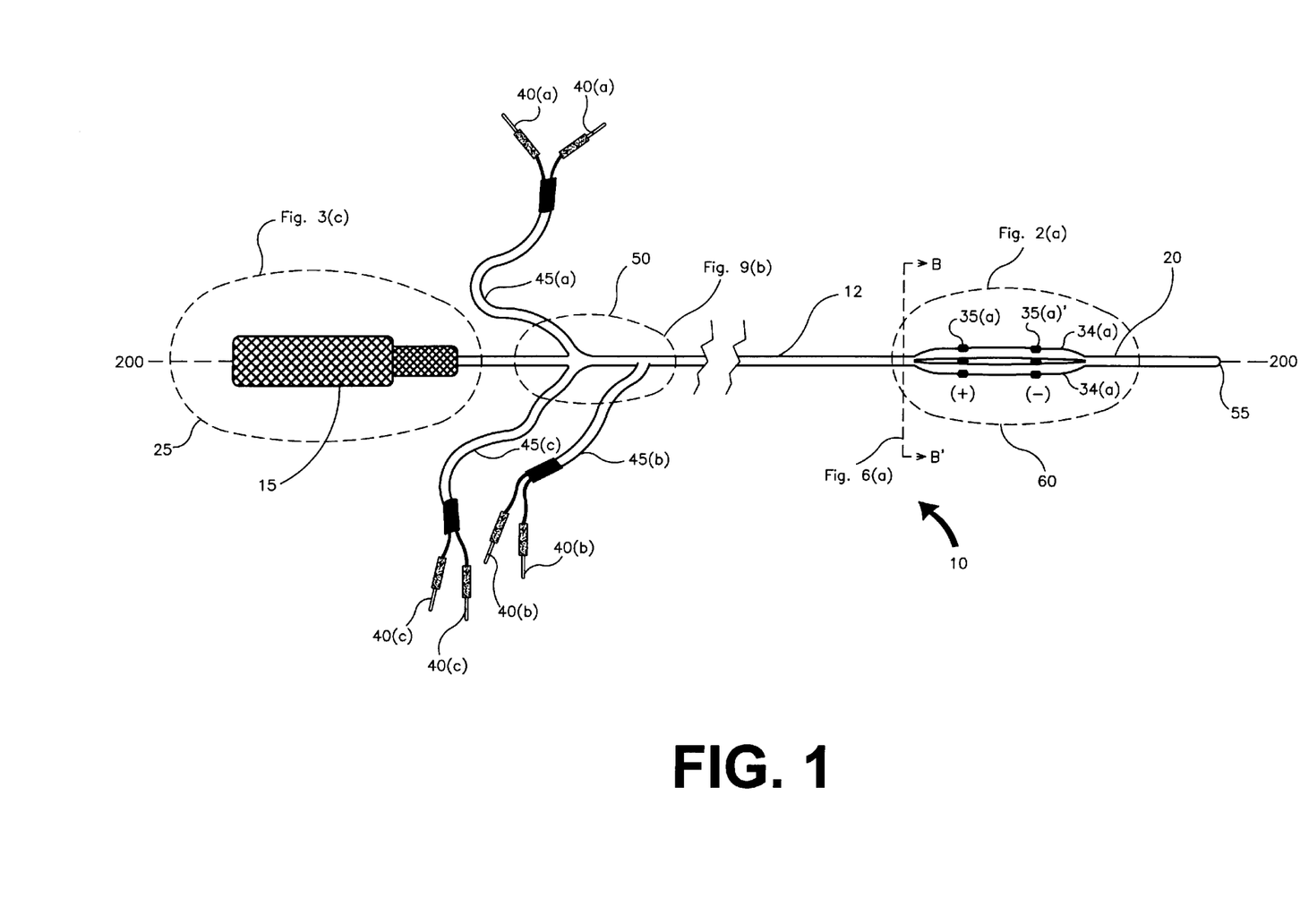
FIG. 1 shows a top plan view of one embodiment of lead 10 of the present invention.

A first embodiment of a mechanically expandable transesophageal medical lead 10 is illustrated in FIG. 1. Medical lead 10 includes an elongated flexible lead body 12 extending between proximal end 15 and distal end 20 and along imaginary axially disposed axis 200. Forming part of, carried on, or attached to or near distal end 20 is distention mechanism 60 comprising a plurality of distention arms 30(a), 30(b) and 30(c). According to the dictates of the precise design at hand, lead 10 may have more or fewer distention arms 30.

Flexible lead body 12 most preferably has a plurality of lumens 110, 120(a), 120(b) and 120(c) disposed therewithin for housing pull wire 65 (not shown in FIG. 1) and electrical conductors 45(a), 45(a)', 45(b), 45(b)', 45(c) and 45(c)' (also not shown in FIG. 1). Lumens 110, 120(a), 120(b) and 120(c) most preferably form elongated axially extending cavities having cylindrical shapes in cross-section, and sufficiently large to accept the aforementioned electrical conductors and pull wire therewithin. Those lumens may or may not extend the entire length of lead 10 between proximal end 15 and distal end 20. Distal end 20 most preferably terminates in a soft bendable deflectable tip 55 that minimizes trauma to tissues of the subject whether medical lead 10 is inserted into the esophagus nasally or orally.

Lead body 12 may be formed of any suitable flexible medical grade rubber, silicon based material or other similar material such as polyurethane, siliastic, rubber or silicone. In use, distal end 20 of esophageal medical lead 10 is positioned in the esophagus of a human subject adjacent a posterior surface of the heart. Proximal end 15 is positioned outside the subject where external connectors 40(a) through 40(c)' are connected to a cardiac stimulating, monitoring or defibrillating apparatus, usually after distention mechanism 60 has been expanded. FIG. 9(b) shows details of conductor branching region 50 of lead 10.

Figures 2A, 2B:
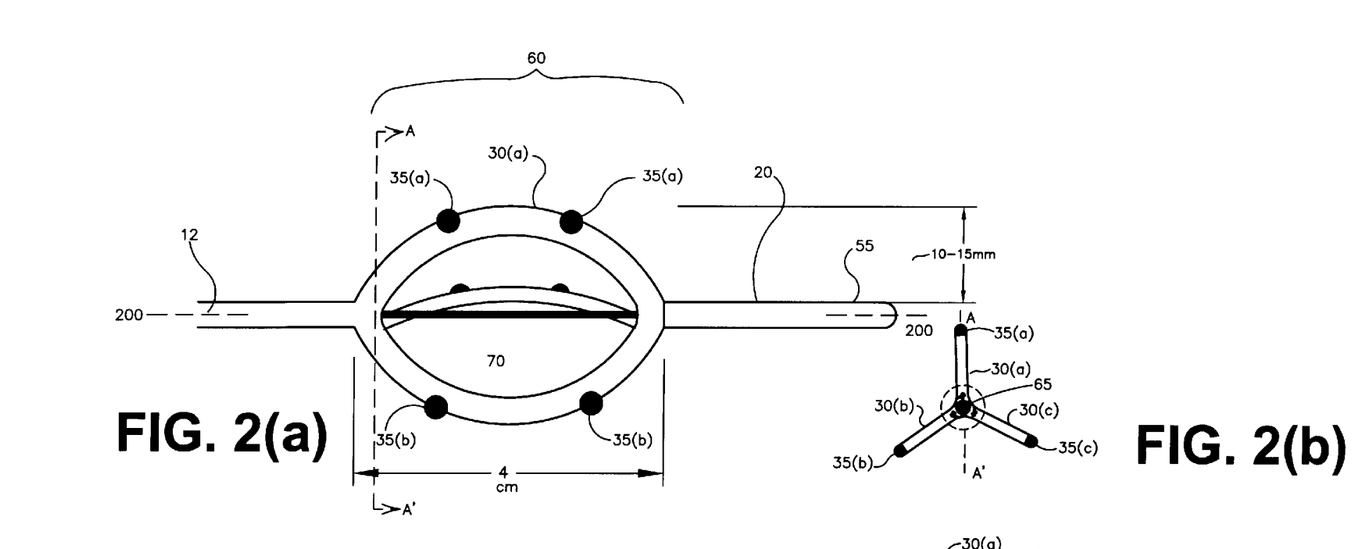
FIGS. 2(a) through 2(d) show further views of selected portions of lead 10 of FIG. 1.
Figure 2C:
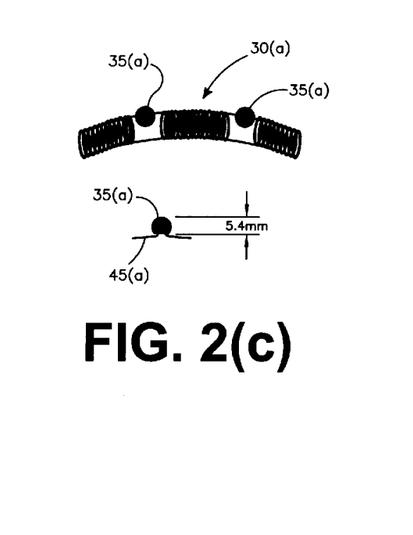

Pairs of external connectors 40(a)–40(a)', 40(b)–40(b)' and 40(c)–40(c)' each typically correspond to discrete sets of monitoring, defibrillating or stimulating electrodes 35(a)–35(a)', 35(b)–35(b)' and 35(c)–35(c)' disposed on distention arms 30(a), 30(b) and 30(c), respectively, and are usually employed in such a configuration. As shown in FIGS. 1, 2(a) and 2(c), electrode pairs 35(a)–35(a)', 35(b)–35(b)' and 35(c)–35(c)' are affixed to distention arms 30(a), 30(b) and 30(c), respectively.

While in the Figures only two electrical conductors (such as 45(a) and 45(a)') are illustrated as corresponding to a single set or pair of electrodes (as, for example, electrodes 35(a) and 35(a)'), it will be understood by those skilled in the art that the exact number of electrodes corresponding to a given number of electrical conductors may be varied and is not intended to constitute a limitation of the present invention. Nor is the shape of such electrodes or conductors intended to constitute a limitation of the present invention. Thus, many other electrical conductor numbers, electrical conductor configurations and shapes, electrode combinations, electrode spacings, numbers of electrodes, electrode configurations and shapes, the electrical interconnections of same (e.g., series or parallel electrical connections, polarity or polarity switching of electrodes, etc.) and numbers of distention arms are contemplated in the present invention.

For example, electrodes 35(a) and 35(a)' could each be split into two portions, or the spacing between electrodes could be varied by switching external connectors. Electrodes 35(a), 35(b) and 35(c) could be electrically configured such that electrode 35(a) operates as a cathode and electrode 35(b) or 35(c) operates as an anode. Three electrodes could be disposed on each arm of distention mechanism 60 such that the central electrode acts as an anode or cathode, while the outside electrodes are characterized in having the opposite polarity (i.e., cathode or anode).

It is an advantage of some embodiments of the present invention that an optimal configuration, array, pair, number or spacing of electrodes may be selected by a user to provide optimal pacing, monitoring or defibrillating of the heart based on the rotary orientation of lead body 12 respecting the heart of a subject.

Pull wire 65 (not shown in FIG. 1) extends through central lumen 110 between proximal end 15 and distal end 20, and effectuates expansion and retraction of distention mechanism 60 after distal end 20 has been positioned within a desired portion of a patient's esophagus. Arms 30(a) through 30(c) most preferably expand symmetrically when retracting pull wire 65 is pulled towards proximal end 15 from distal end 20 by pull wire axial movement mechanism 60. FIG. 2(a) shows mechanism 60 in an at least partially distended or fully distended state. In a fully distended state, arms 30(a) through 30(c) most preferably extend outwardly about 10 to 15 millimeters from the external surface of lead body 12.

As shown in FIGS. 2(a) through 2(c), when arms 30(a) through 30(c) are extended, stiffening mechanism 70 becomes more readily visible. Stiffening mechanism 70 provides the amount of structural compression required in the immediate region of distention mechanism 60 to prevent arms 30(a) through 30(c) from all bowing outwardly to one side or another when pull wire 65 is retracted by pull wire axial movement mechanism 25. Distention mechanism 60, which most preferably, but not necessarily, includes stiffening mechanism 70, causes arms 30(a) through 30(c) to expand laterally and symmetrically or asymmetrically in respect of lead body 12 when pull wire 65 is retracted.

Those skilled in the art will understand that variations may be made in coil 75, stiffening mechanism 70, distention mechanism 60, arms 30 and pull wire axial movement mechanism 25 without departing from the spirit and scope of the present invention. For example, stiffening mechanism 70 may comprise more or fewer sleeves 90, 95 and 100, pull wire 65 may be pushed by a user to expand distention mechanism 60 by appropriately adapting the structural configuration of pull wire axial movement mechanism 25, lead body 12 and distention mechanism 60, or coil 75 may comprise more or fewer than four filars.

Figure 2D:
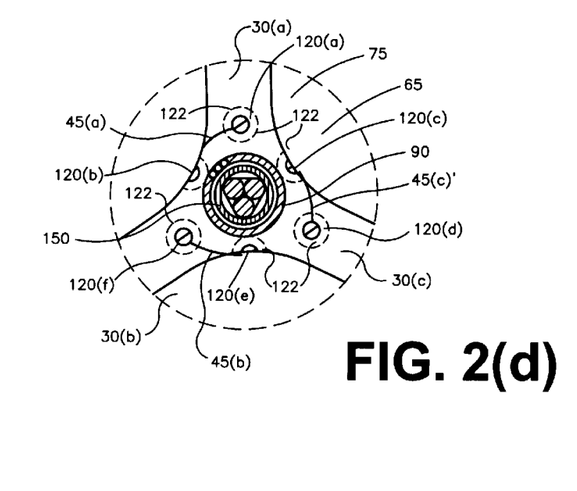

FIG. 2(b) shows a cross-sectional view of lead 10 through axis A–A' of FIG. 2(a), where arms 30 are expanded outwardly away from the central axis of lead body 12. FIG. 2(d) shows a detailed view of the central region of lead 10 shown in FIG. 2(b), where four-filar coil 75 most preferably sheathes centrally disposed and FEP-insulated pull wire 65. Coil 75 provides an important advantage of the present invention, namely providing the capability of transferring a substantial or significant amount of torque or rotational movement from proximal end 15 of lead 10 to distal end 20, thereby permitting highly accurate positioning or location of electrodes 35 in the esophagus of a patient.

In that portion of distention mechanism 60 nearest proximal end 15, electrical conductors 45(a)', 45(b)' and 45(c)' are most preferably routed from lumens 120(b), 120(e) and 120(c), respectively, into lumens 120(a), 120(f) and 120(d), respectively, which in turn are already occupied by electrical conductors 45(a), 45(b) and 45(c), respectively. Electrical conductors 45 are most preferably formed of medical grade stainless steel and insulated with an appropriate biostable, biocompatible electrical insulator. Pull wire 65 is most preferably sheathed in PTFE or other appropriate coating 150 to facilitate sliding within lumen 110. Coating 150 is shown disposed between the inner surface of coil 75 and the outer surface of pull wire 65. Pull wire 65 is most preferably formed of a plurality of individual medical grade stainless steel wires twisted, stranded or braided together. In preferred embodiments of the present invention, nineteen such wires are stranded together to form pull wire 65.

Figure 3A:
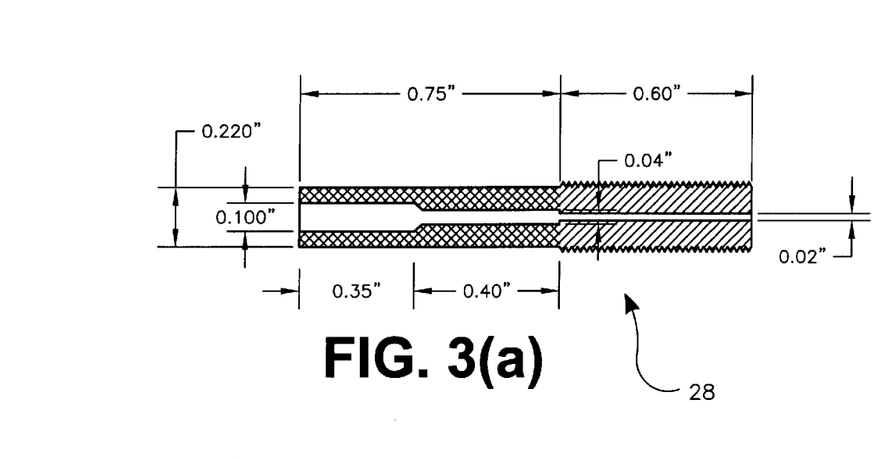
FIGS. 3(a) through 3(c) show selected cross-sectional views of various portions of pull wire axial movement mechanism 25 of FIG. 1.
Figure 3B:
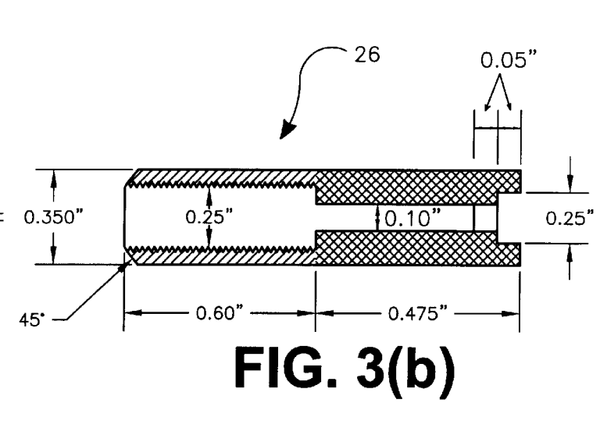
Figure 3C:
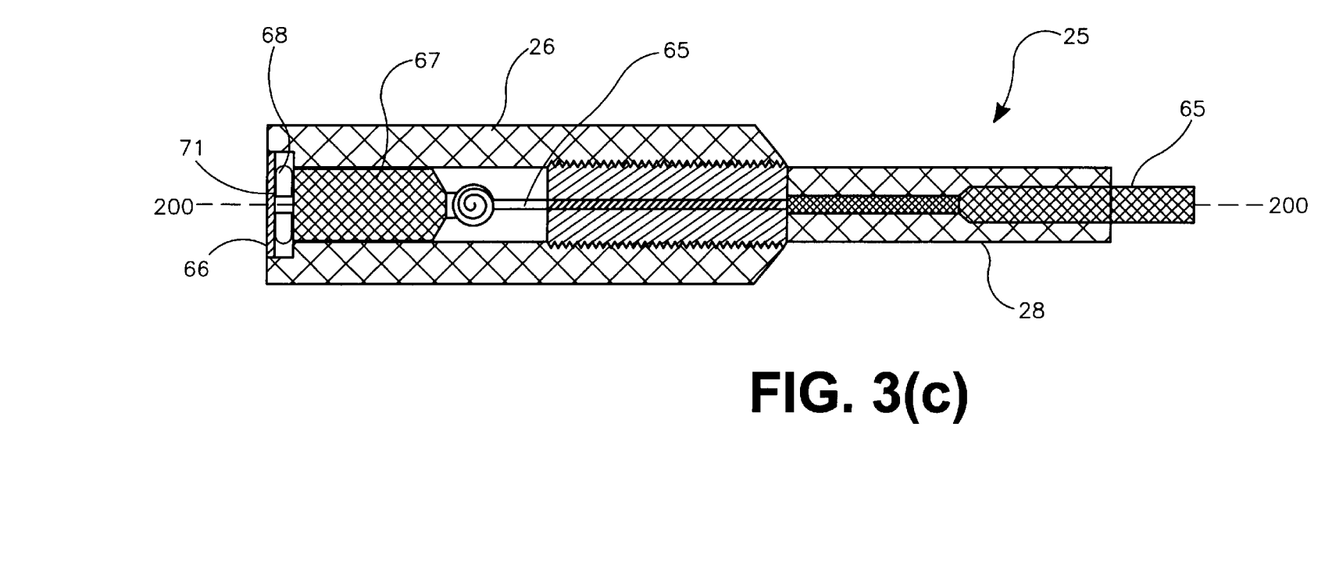

FIGS. 3(a) through 3(c) show various cross-sectional views of one embodiment of pull wire axial movement mechanism 25 of the present invention, where pull wire 65 is retracted by turning rotating pull wire mechanism 26 in a first direction with respect to the proximal end of stationary pull wire mechanism 28. In so doing, proximal end 71 of pull wire 65 is retracted towards proximal end 15, and distention mechanism 60 expands outwardly and laterally away from lead body 12. Ball bearing swivel 67 is rotatably mounted to proximal end 67 by means of locking pin 68. Proximal end cap 66 provides a seal for rotating pull wire mechanism 26. Turning rotating pull wire mechanism 26 in a second direction opposite from the first direction with respect to the proximal end of stationary pull wire mechanism 28 causes distention mechanism 60 to retract inwardly towards lead body 12.

In practice, when distention mechanism 60 is emplaced in the esophagus of a patient retraction thereof may be accomplished by merely releasing pull wire 65 owing to the collapsing forces exerted on mechanism 60 by muscles formed in or adjacent to the esophageal wall. Furthermore, pull wire axial movement mechanism 25 of the present invention may assume any of a number of different structural configurations such as a proximal end of a pull wire that is simply grasped and pulled by a user, a mechanism that is compressed or pulled apart by a user, or a mechanism having a pull wire that is pushed by a user to cause distention mechanism 60 to expand away from lead body 12. The actuating directions, methods and structures of pull wire axial movement mechanism 25 may be changed without departing from the spirit and scope of the present invention.

FIG. 2(c) shows one means of structurally reinforcing arms 30 of the present invention by wrapping "spider ice line wire" or other appropriate material 105 around the outer surface of arms 30. "Spider ice line wire" is formed of high molecular weight polyethylene, and imparts additional strength to arms 30 after electrodes 35 have been attached thereto. As shown in FIG. 2(c), single electrical conductor 45(a) is attached to the underside of electrode 35, the distal end of conductor 45(a) most preferably extending distally from such underside for reasons that become apparent below.

In preferred embodiments of the present invention each electrode is coupled by an elongated conductive wire or conductor 45(a), 45(a)', 45(b), 45(b)', 45(c) and 45(c)' disposed within lead body 12 to its respective external connector 40(a), 40(a)', 40(b), 40(b)', 40(c) or 40(c)', where the external connectors are located adjacent proximal end 15 of medical lead 10. The conductors are preferably disposed in lumens 120(a), 120(b), 120(c), 120(d), 120(e) and 120(f). Alternatively, fewer lumens may house more conductors within lead body 12, or much less preferably the conductors may be attached by various means and in various configurations to the outer surface of lead body 12.

Figure 4A:
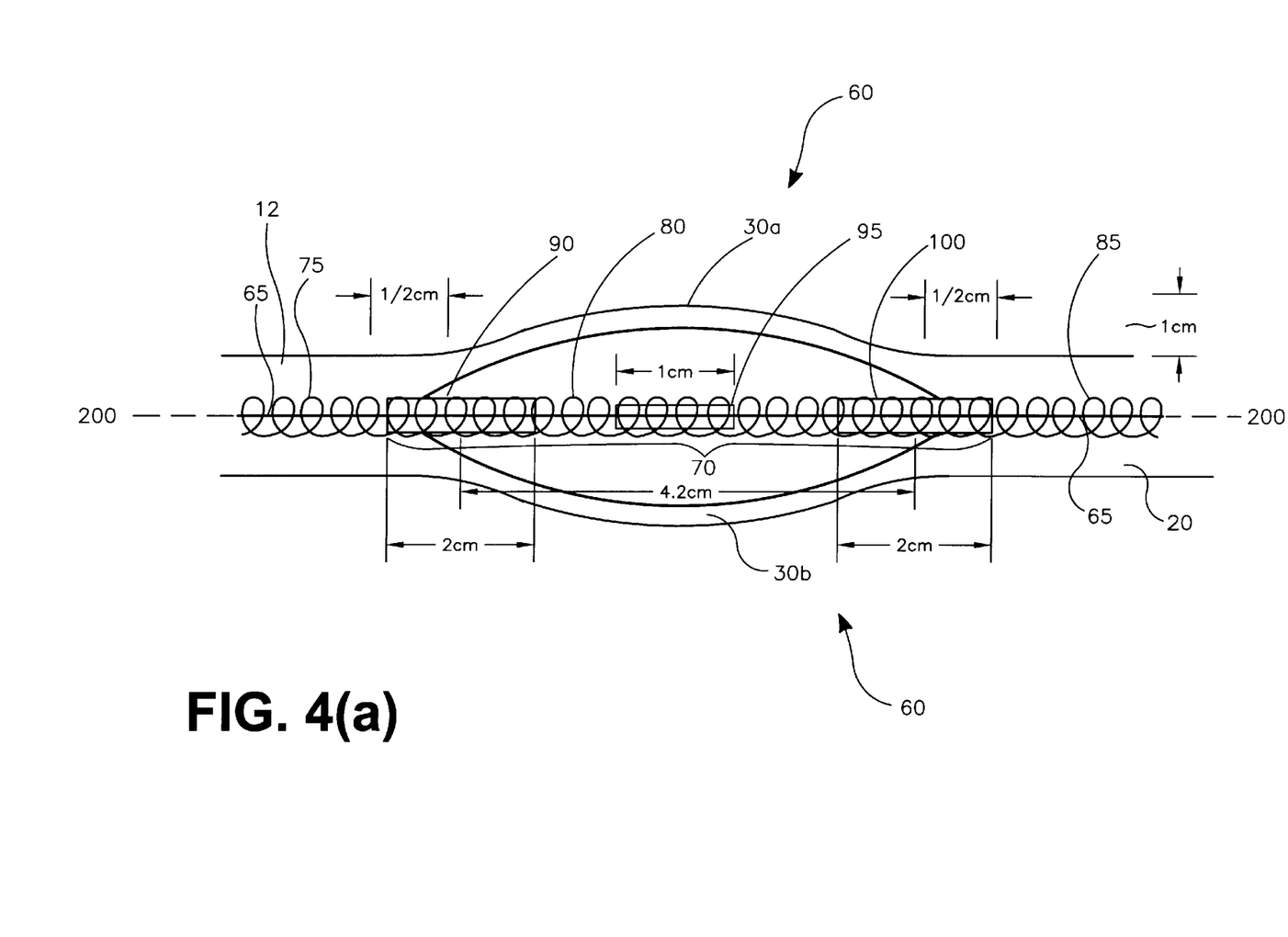
FIGS. 4(a) and 4(b) show two embodiments of distention mechanism 60 of the present invention.
Figure 4B:
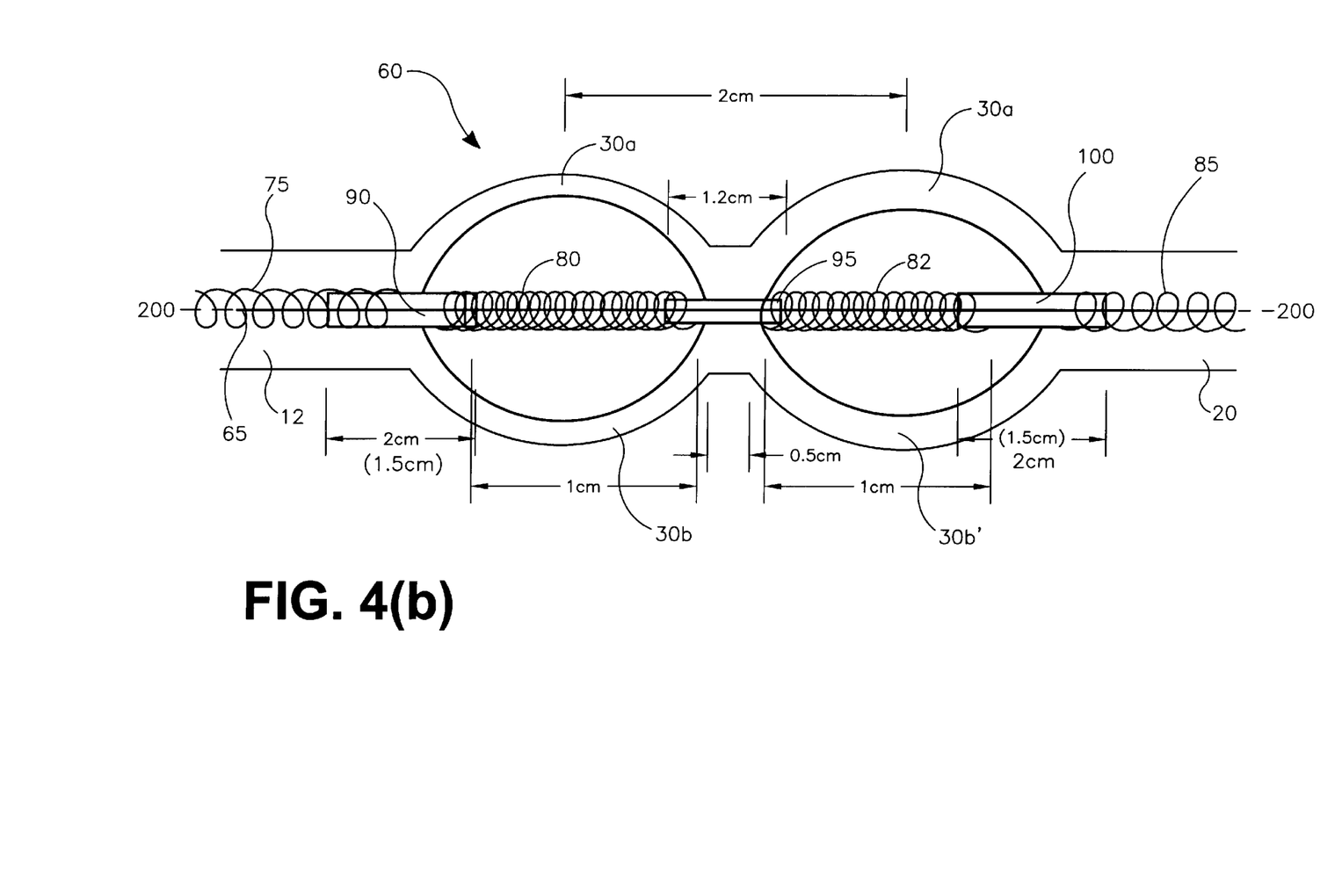

Distention mechanism 60 illustrated in FIGS. 4(a) and 4(b) includes a plurality of arms 30(a), 30(b) and 30(c) responsive to movement of pull wire 65 disposed within lead body 12 and stiffening mechanism 70 by causing distention mechanism 60 to expand or retract. Arms 30(a), 30(b) and 30(c) are all mechanically coupled together at the proximal and distal ends of distention mechanism 60, most preferably by emplacing coils around lead body 12 at the distal and proximal ends of distention mechanism 60, and crimping the coils to lead body 12 using a 4-point crimp tool.

Figure 5:
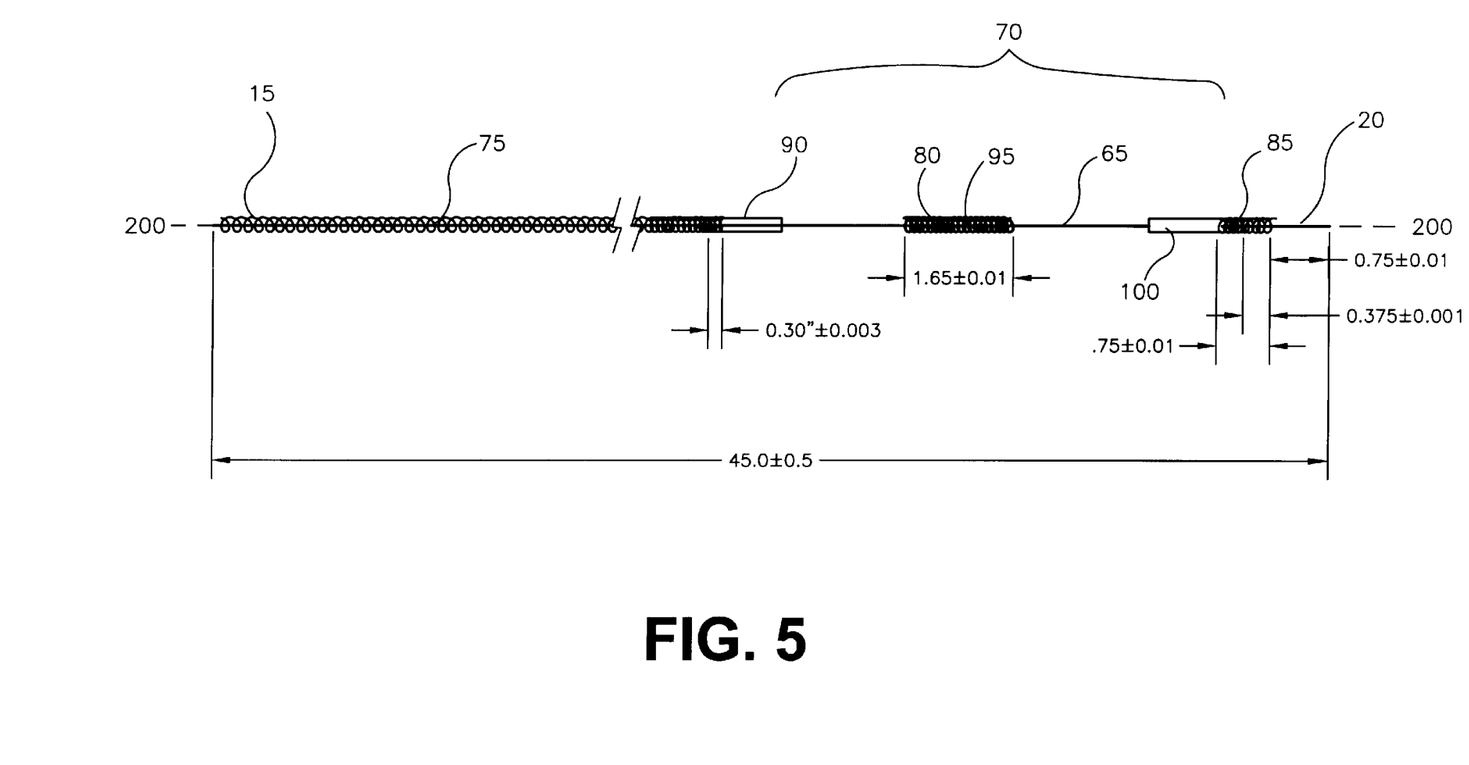
FIG. 5 shows one embodiment of stiffening mechanism 70 of the present invention.

The various components of stiffening mechanism 70 illustrated in FIG. 5 are most preferably crimped together first, followed by mechanism 70 being inserted in lumen 110 while lumen 110 is dilated by soaking lead body 12 in acetone. Upon removal from the acetone, lead body 12 shrinks and lumen 110 compresses against the proximal and distal ends of stiffening mechanism 70.

Distention mechanism 60 illustrated in FIGS. 4(a) and 4(b) most preferably expands symmetrically with respect to lead body 12 in combination with conductors 45(a), 45(a)', 45(b), 45(b)', 45(c) and 45(c)'. It will be understood that a distention mechanism that expands in a non-symmetric manner may be employed as an alternative to the plurality of arms 30(a), 30(b) and 30(c).

Mechanism 60 illustrated in FIG. 4(b) shows one embodiment of lead 10 of the present invention where two separate expandable and retractable structures form a portion of distal end 20 of lead 10. Each such expandable and retractable structure may have one, a pair or more electrodes attached to each of the expandable and retractable arms thereof.

Note that the dimensions of the various components illustrated in FIGS. 4(a) and 4(b), and in other Figures set forth herein, are merely preferred dimensions employed by the inventors during the process of reducing the present invention to practice. Those dimensions are merely illustrative and constitute no limitation respecting the various embodiments of the present invention. That is, significant variations may be made to the dimension set forth herein without departing from the spirit and scope of the present invention.

FIGS. 4(a) through 5 show some details of stiffening mechanism 70 comprising proximal end coil 75, distal end coil 85, distention mechanism coil 80 and/or 82, proximal sleeve 90, middle sleeve 95 and distal sleeve 100. FIG. 5 shows one embodiment of stiffening mechanism 70 of the present invention; note that other embodiments of the stiffening mechanism 70 that perform the same stiffening function are contemplated in the present invention.

In FIGS. 4(a) through 5, sleeves 90, 95 and 100 are most preferably formed of medical grade stainless steel needle tubing. Coils 75, 80, 82 and 85 are most preferably formed of medical grade four-filar helically wound stainless steel. The distal end of lead body coil 75 is attached to the proximal end of proximal sleeve 90 by crimping or other means. Likewise, the various respective distal and proximal ends of coils 80, 82 and 85 are crimped to their respective sleeves in similar fashion.

As pull wire 65 is retracted axially by a user, sleeves 90, 95 and 100 are drawn ever closer to one another until distention mechanism 60 achieves a requisite amount of outward expansion to permit the sleeves to form a substantially rigid structure permitting arms 30 to expand outwardly without collapsing in an undesired direction or orientation. When distention mechanism 60 is contracted or collapsed by releasing pull wire 65 towards distal end 20, sleeves 90, 95 and 100 pull apart from one another, thereby changing the structurally rigid or substantially rigid expanded state characterizing distention mechanism 60 to a state characterized by limpness or flexibility respecting distention mechanism 60, the state of flexibility so achieved most preferably being sufficient to permit mechanism 60 to be withdrawn or inserted transnasally or transorally in a human subject. In practice, when distention mechanism 60 is emplaced in the esophagus of a patient retraction thereof may be accomplished by merely releasing pull wire 65 owing to the collapsing forces exerted on mechanism 60 by muscles formed in or adjacent to the esophageal wall.

FIGS. 6(a) through 6(d) show selected cross-sectional views of various embodiments of lead body 12 in the vicinity of distention mechanism 60. As shown in those Figures, cuts or slices 140(a), 140(b) and 140(c) may transect lumens disposed within lead body 12, or may alternatively be disposed between lumens.

Figure 6A:
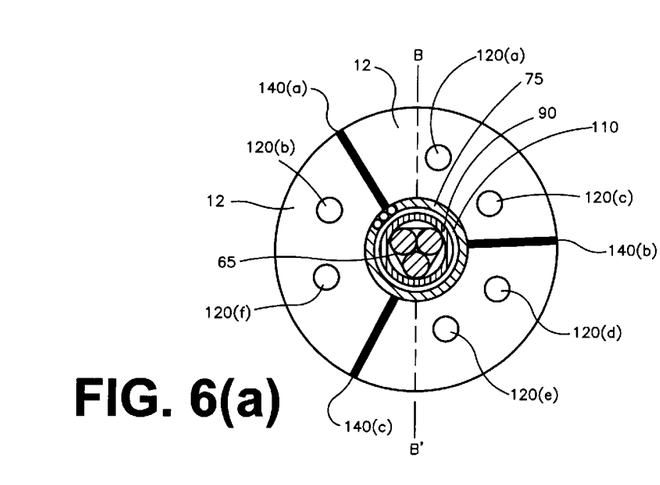
FIGS. 6(a) through 6(d) show selected cross-sectional views of various embodiments of lead body 12 in the vicinity of distention mechanism 60.
Figure 6B:
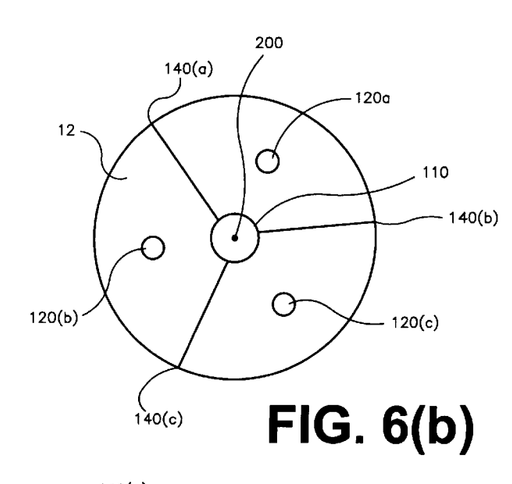
Figure 6C:
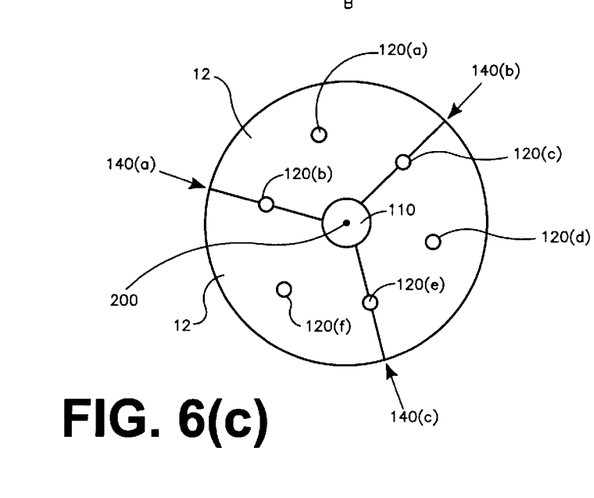

A variable number of lumens may be disposed within lead bodies 12 of the present invention. For example, as shown in FIG. 6(b), three lumens 120(a) through 120(c) may be formed in lead body 12 by cuts 14(a), 140(b) and 140(c) to carry pairs of insulated electrical conductors 45(a)–45(a)', 45(b)–45(b)' and 45(c)–45(c)' therewithin.

Figure 6D:
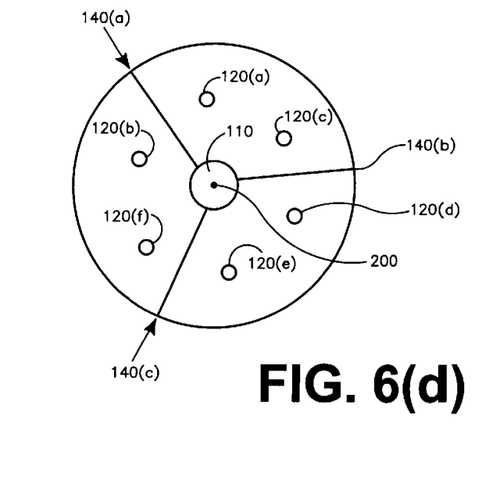
Figure 9A:
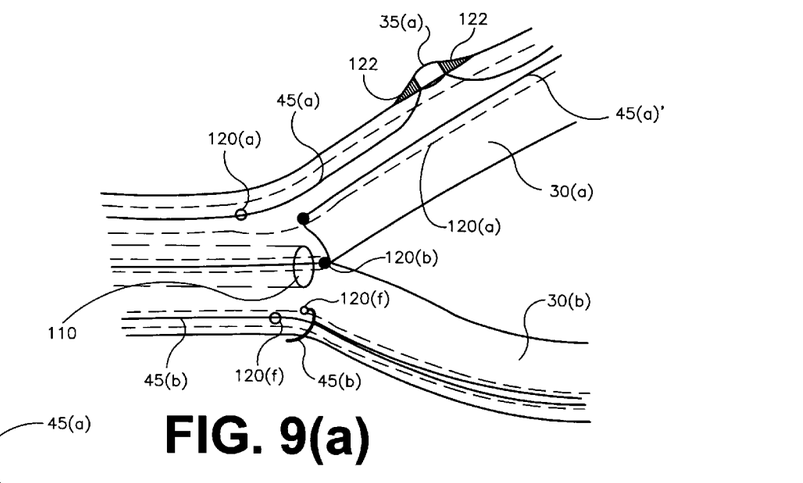
FIGS. 9(a) and 9(b) show various examples of the means by which electrical conductors may be routed from lead body 12 to distention arms 30 or external connectors 40 of the present invention.
Figure 9B:
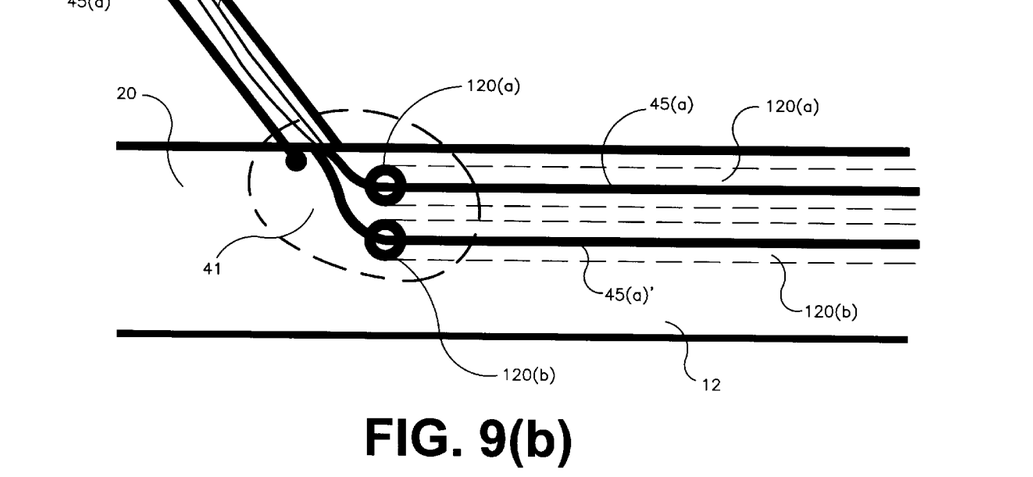

More preferably and alternatively, and as illustrated in FIGS. 6(d), 2(d) and 9(a), insulated electrical conductors 45(a), 45(a)', 45(b), 45(b)', 45(c) and 45(c)' are each housed in separate lumens 120(a) through 120((f) between proximal end 15 and distention mechanism 60. At the proximal end of distention mechanism 60, and moving in a direction from the proximal end of distention mechanism 60 towards the distal end of distention mechanism 60, conductors 45(a)', 45(b)' and 45(c)' are rerouted from their separate lumens into the lumens housing conductors 45(a), 45(b) and 45(c), respectively. It has been discovered that this alternative embodiment of the present invention prevents undesirable coiling of lead 10 and permits easier placement and routing of the conductors within lumens than would otherwise be possible.

It has also been discovered that the conductors are most easily placed in and routed through their respective lumens when lead body 12 is formed of polyurethane by soaking lead body 12 in acetone, slipping the conductors through their respective lumens while lead body 12 is immersed in the acetone, and removing lead 10 from the acetone upon completing conductor emplacement in lead body 12. If lead body 12 is formed of silicon, lead body 12 may be soaked in FREON to achieve the same results respecting emplacement of the conductors in their respective lumens in lead body 12.

Lead body 12 is most preferably cut by forming notches at each end of the portion of lead body 12 to be cut and to a depth necessary to access the lumen of interest, slipping a stainless steel wire of sufficiently small diameter between the notches, and pulling the wire upwardly and laterally along the selected lumen to slice lead body 12 open.

Figure 7A:
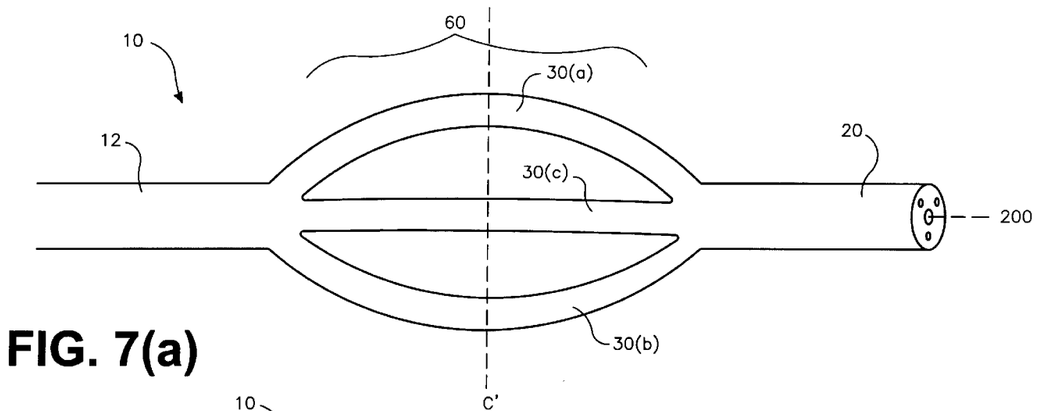
FIGS. 7(a) and 7(b) show perspective views of distal end 20 of lead 10, and a manner in which lead body 12 may be sliced open to form arms 30(a) through 30(c) of the present invention.
Figure 7B:
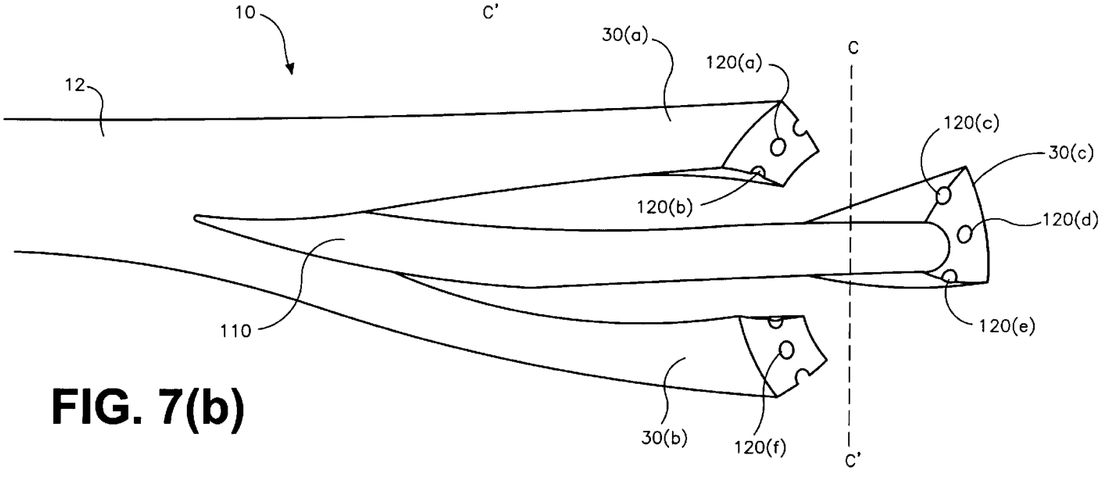

FIGS. 7(a) and 7(b) show perspective views of one embodiment of distal end 20 of lead 10 of the present invention, and a manner in which lead body 12 may be sliced open to form arms 30(a) through 30(c) by having cuts or slices 140(a), 140(b) and 140(c) transect lumens 120(b), 120(e) and 120(c),, respectively.

FIG. 9(b) shows details of one embodiment of branching region 50, where a pair of electrical conductors 45(a) and 45(a)' emerge from lumens 120(a) and 120(b) and lead body 12 for connection to external connectors 40(a) and 40(b).

Those skilled in the art will now understand that the precise number, positioning and diameter of the various lumens of the present invention may be varied according to the particular application and lead design under consideration.

Figures 8A, 8B, 8C:
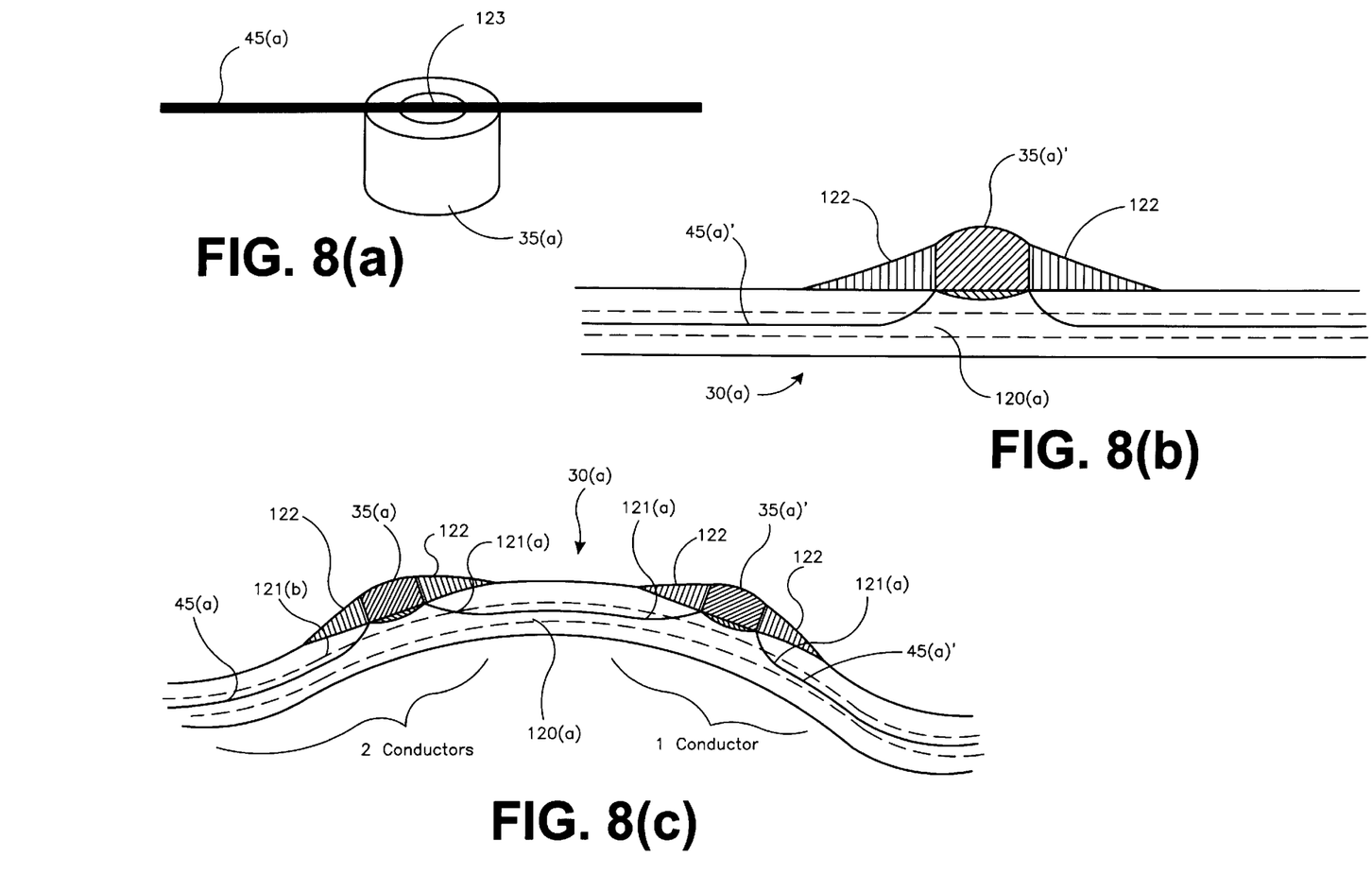
FIGS. 8(a) through 8(b) show perspective and cross-sectional views of a selected embodiment of electrodes 35(a) and 35(a)' and distention arm 30(a) of the present invention.

FIGS. 8(a) through 8(b) show perspective and cross-sectional views of a selected embodiment of electrodes 35(a) and 35(a)' and distention arm 30(a) of the present invention, and a preferred method of securing electrodes 35 to arms 30. FIG. 8(a) shows solder connection 123 attaching electrode 35(a) to electrical conductor 45(a). Note that it is preferred for the distal end of conductor 45(a) or 45(a)' to extend distally beyond electrode 35(a) or 35(a)' for subsequent placement in that portion of lumen 120(a) located distally from electrode 35(a) or 35(a)'.

As illustrated in FIGS. 8(b) and 8(c), electrodes 35(a) and 35(a)' are preferably mounted to arm 30(a) by forming respective slits to a depth corresponding to the position of lumen 120(a), placing the electrode in the slit, and disposing an appropriate biostable, biocompatible medical grade adhesive 122 about the sides of the electrodes. As shown in FIG. 8(c), it is preferred that two electrical conductors 45(a) and 45(a)' be disposed in lumen 120(a) between the proximal end of distention mechanism 60 and electrode 35(a), and that one electrical conductor 45(a)' be disposed in lumen 120(a) between electrode 35(a) and electrode 35(a)'. Those skilled in the art will now understand that the precise number, positioning and means of mounting electrodes 35 and conductors 45 to lead body 12 or arms 30 of the present invention may be varied according to the particular application and lead design under consideration.

Figure 10A:
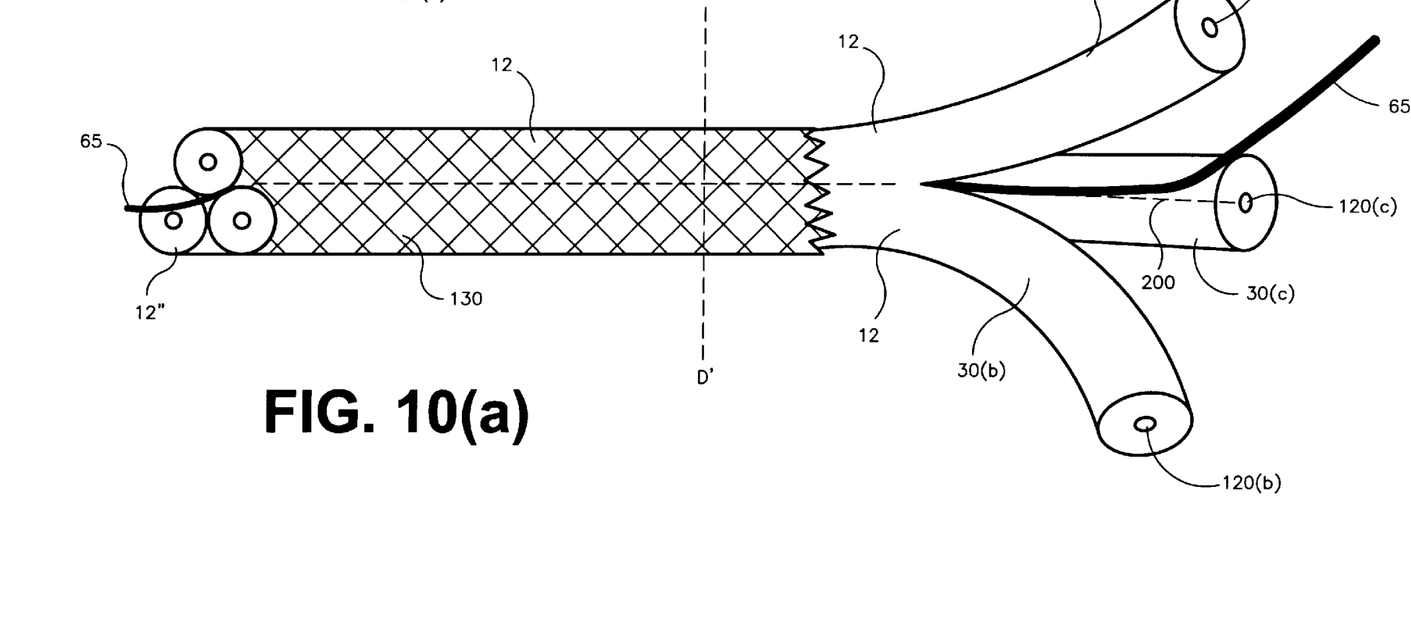
FIGS. 10(a) and 10(b) show an alternative embodiment of lead 10 of the present invention.
Figure 10B:
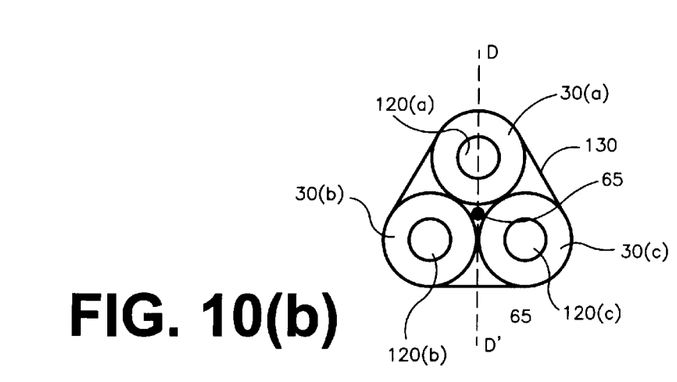

FIGS. 10(a) and 10(b) show an alternative embodiment of lead 10 of the present invention formed from three separate lead bodies 12, 12' and 12", each such lead body having one centrally located lumen disposed therewithin. Pull wire 65 is housed in the space defined by the internal juncture of the three lead bodies. Braided sheath 130 is disposed about the three lead bodies to provide a means of securing the lead bodies to one another and for permitting torque to be transferred between the proximal and distal ends of lead 10. Braided sheath 130 is preferably covered by a suitable heat shrink or other pliable, biostable and biocompatible material that will not damage esophageal tissues. Arms 30(a), 30(b) and 30(c) of distention mechanism 60 are formed by terminating sheath 130 at an appropriate location near the proximal end of distention mechanism 60, and by positioning another proximal sheath at a location disposed distally from distention mechanism 60.

The scope of the present invention is not limited to pacing, monitoring or sensing applications, but extends to defibrillation, cardiac mapping and other medical and medical device applications and methods. Nor is the scope of the present invention limited to applications where a human heart is sensed, monitored, paced, or defibrillated, but instead includes similar applications in other mammalians and mammalian organs.

The preceding specific embodiments are illustrative of the practice of the invention. It is to be understood, therefore, that other expedients known to those skilled in the art or disclosed herein, may be employed without departing from the invention or the scope of the appended claims.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents listed in Table 1 or elsewhere hereinabove are hereby incorporated by reference into the specification hereof, each in its respective entirety.

We claim:

1. A transesophageal medical lead, comprising:
   (a) an elongated, flexible lead body having first proximal and first distal ends, the lead body having a plurality of elongated lumens disposed therewithin and extending at least substantially between the first distal and first proximal ends of the lead body;
   (b) at least one external electrical connector;
   (c) a pull wire having second distal and second proximal ends, the pull wire being slidably disposed in a first of the plurality of lumens, the second distal end of the pull wire being fixedly attached at or near the first distal end of the lead body;
   (d) at least one electrical conductor having third distal and third proximal ends and disposed in a second of the plurality of lumens, the third proximal end of the at least one electrical conductor being mechanically and electrically connected to the at least one external electrical connector;
   (e) a distention mechanism located at or near the first distal end of the lead body, comprising:
       (1) at least one flexible arm having at least one cardiac sensing, monitoring or defibrillating electrode disposed or mounted thereon, the at least one electrode being mechanically and electrically connected to a point at or near the third distal end of the at least one electrical conductor;
       (2) a stiffening mechanism having a central axially-extending aperture disposed therewithin, the pull wire slidably engaging and passing through the central aperture of the stiffening mechanism;
   wherein the distention mechanism is laterally expandable and retractable respecting the lead body through retraction of the pull wire by a user, the stiffening mechanism providing the amount of structural compression required in the region of the distention mechanism to prevent the at least one arm from bowing outwardly in an undesired direction or orientation when the pull wire is retracted by the user, the medical lead being transnasally or transorally insertable in an esophagus of a subject when the distention mechanism is retracted.

2. The medical lead of claim 1, wherein the distention mechanism includes at least two flexible arms, each arm having at least one cardiac sensing, monitoring or defibrillating electrode disposed or mounted thereon, each electrode being mechanically and electrically connected to a corresponding electrical conductor disposed in one of the plurality of lumens, the proximal end of each corresponding electrical conductor being mechanically and electrically connected to a corresponding external electrical connector, the distal end or a point near the distal end of each corresponding electrical conductor being electrically and mechanically connected to its corresponding electrode.

3. The medical lead of claim 2, wherein each arm has a plurality of electrodes attached thereto or mounted thereon.

4. The medical lead of claim 1, wherein the spacing between electrodes may be varied by selecting appropriate external connectors.

5. The medical lead of claim 1, wherein the distention mechanism includes at least three flexible arms, each arm having at least two cardiac sensing, monitoring or defibrillating electrodes disposed or mounted thereon, each electrode being mechanically and electrically connected to a corresponding electrical conductor disposed in one of the plurality of lumens, the proximal end of each corresponding electrical conductor being mechanically and electrically connected to a corresponding external electrical connector, the distal end or a point near the distal end of each corresponding electrical conductor being electrically and mechanically connected to its corresponding electrode.

6. The medical lead of claim 5, wherein the spacing between electrodes may be varied by selecting appropriate external connectors.

7. The medical lead of claim 1, wherein the lead body comprises at least one of polyurethane, silicone, silastic and rubber.

8. The medical lead of claim 1, wherein the pull wire axial movement mechanism comprises a rotating pull wire mechanism and a stationary pull wire mechanism.

9. The medical lead of claim 1, wherein the stiffening mechanism comprises at least one sleeve and at least one coil.

10. The medical lead of claim 1, wherein the stiffening mechanism comprises a proximal end coil, a distal end coil and a distention mechanism coil.

11. The medical lead of claim 1, wherein the stiffening mechanism comprises a proximal sleeve, a middle sleeve and a distal sleeve.

12. The medical lead of claim 1, wherein a lead body coil extends between at least substantial portions of the distal and proximal ends of the lead body, the lead body coil being disposed within the first of the plurality of lumens, the lead body coil permitting the transfer of a substantial amount of torque from the proximal end of the lead to the distal end of the lead.

13. The medical lead of claim 12, wherein the lead body coil has a central lumen disposed therewithin, the pull wire being disposed within at least portions of the central lumen of the lead body coil.

14. The medical lead of claim 1, wherein the distention mechanism expands or retracts symmetrically or asymmetrically.

15. A transesophageal medical lead, comprising:
(a) means for forming an elongated, flexible lead body having first proximal and first distal ends, the lead body forming means having a plurality of means for forming elongated lumens disposed therewithin and extending at least substantially between the first distal and first proximal ends of the lead body forming means;
(b) at least one external means for electrically connecting;
(c) means for pulling having second distal and second proximal ends, the pulling means being slidably disposed in a first of the plurality of lumen forming means, the second distal end of the pulling means being fixedly attached at or near the first distal end of the lead body forming means;
(d) at least one means for conducting electricity having third distal and third proximal ends and disposed in a second of the plurality of lumen forming means, the third proximal end of the at least one electricity conducting means being mechanically and electrically connected to the at least one external electrically connecting means;
(e) a means for distending located at or near the first distal end of the lead body forming means, comprising:
(1) at least one flexible rib means having at least one means for sensing, monitoring or defibrillating disposed or mounted thereon, the at least one sensing means being mechanically and electrically connected to a point at or near the third distal end of the at least one electricity conducting means;
(2) a means for stiffening having a central axially-extending aperture disposed therewithin, the pulling means slidably engaging and passing through the central aperture of the stiffening means;
wherein the distending means is laterally expandable and retractable respecting the lead body forming means through retraction of the pulling means by a user, the stiffening means providing the amount of structural compression required in the region of the distending means to prevent the at least one rib means from bowing outwardly in an undesired direction or orientation when the pulling means is retracted by the user, the medical lead being transnasally or transorally insertable in an esophagus of a subject when the distending means is retracted.

16. The medical lead of claim 15, wherein the distending means includes at least two flexible rib means, each rib means having at least one sensing, monitoring or defibrillating means disposed or mounted thereon, each sensing, monitoring or defibrillating means being mechanically and electrically connected to a corresponding electricity conducting means disposed in one of the plurality of lumen forming means, the proximal end of each corresponding electricity conducting means being mechanically and electrically connected to a corresponding external means for electrically connecting, the distal end or a point near the distal end of each corresponding electricity conducting means being electrically and mechanically connected to its corresponding sensing, monitoring or defibrillating means.

17. The medical lead of claim 16, wherein each rib means has a plurality of sensing, monitoring or defibrillating means attached thereto or mounted thereon.

18. The medical lead of claim 15, wherein the spacing between sensing, monitoring or defibrillating means may be varied by selecting appropriate external means for electrically connecting.

19. The medical lead of claim 15, wherein the distending means includes at least three flexible rib means, each rib means having at least two sensing, monitoring or defibrillating means disposed or mounted thereon, each sensing, monitoring or defibrillating means being mechanically and electrically connected to a corresponding electricity conducting means disposed in one of the plurality of lumen forming means, the proximal end of each corresponding electricity conducting means being mechanically and electrically connected to a corresponding external means for electrically connecting, the distal end or a point near the distal end of each corresponding electricity conducting means being electrically and mechanically connected to its corresponding sensing, monitoring or defibrillating means.

20. The medical lead of claim 19, wherein the spacing between sensing, monitoring or defibrillating means may be varied by selecting appropriate external means for electrically connecting.

21. The medical lead of claim 15, wherein the lead body forming means comprises at least one of polyurethane, silicone, silastic and rubber.

22. A method of making a transesophageal medical lead, the medical comprising an elongated, flexible lead body having first proximal and first distal ends, the lead body having a plurality of elongated lumens disposed therewithin and extending at least substantially between the first distal and first proximal ends of the lead body, at least one external electrical connector, a pull wire having second distal and second proximal ends, the pull wire being slidably disposed in a first of the plurality of lumens, the second distal end of the pull wire being fixedly attached at or near the first distal end of the lead body, at least one electrical conductor having third distal and third proximal ends and disposed in a second of the plurality of lumens, the third proximal end of the at least one electrical conductor being mechanically and electrically connected to the at least one external electrical connector, a distention mechanism located at or near the first distal end of the lead body, the distention mechanism comprising at least one flexible arm having at least one cardiac sensing, monitoring or defibrillating electrode disposed or mounted thereon, the at least one electrode being mechanically and electrically connected to a point at or near the third distal end of the at least one electrical conductor, the distention mechanism further comprising a stiffening mechanism having a central axially-extending aperture disposed therewithin, the pull wire slidably engaging and passing through the central aperture of the stiffening mechanism, the distention mechanism being laterally expandable and retractable respecting the lead body through retraction of the pull wire by a user, the stiffening mechanism providing the amount of structural compression required in the region of the distention mechanism to prevent the at least one arm from bowing outwardly in an undesired direction or orientation when the pull wire is retracted by the user, the medical lead being transnasally or transorally insertable in an esophagus of a subject when the distention mechanism is retracted, the method comprising the steps of:

(a) providing the lead body;

(b) providing the at least one external electrical connector;

(c) providing the pull wire;

(d) providing the at least one electrical conductor;

(e) providing the distention mechanism having the at least one flexible arm, the at least one cardiac sensing, monitoring or defibrillating electrode disposed or mounted thereon, and the stiffening mechanism, and (f) assembling the lead body, the at least one external electrical connector, the pull wire, the at least one electrical conductor, and the distention mechanism to form the medical lead.

23. A method of using a transesophageal medical lead in a patient, the medical comprising an elongated, flexible lead body having first proximal and first distal ends, the lead body having a plurality of elongated lumens disposed therewithin and extending at least substantially between the first distal and first proximal ends of the lead body, at least one external electrical connector, a pull wire having second distal and second proximal ends, the pull wire being slidably disposed in a first of the plurality of lumens, the second distal end of the pull wire being fixedly attached at or near the first distal end of the lead body, at least one electrical conductor having third distal and third proximal ends and disposed in a second of the plurality of lumens, the third proximal end of the at least one electrical conductor being mechanically and electrically connected to the at least one external electrical connector, a distention mechanism located at or near the first distal end of the lead body, the distention mechanism comprising at least one flexible arm having at least one cardiac sensing, monitoring or defibrillating electrode disposed or mounted thereon, the at least one electrode being mechanically and electrically connected to a point at or near the third distal end of the at least one electrical conductor, the distention mechanism further comprising a stiffening mechanism having a central axially-extending aperture disposed therewithin, the pull wire slidably engaging and passing through the central aperture of the stiffening mechanism, the distention mechanism being laterally expandable and retractable respecting the lead body through retraction of the pull wire by a user, the stiffening mechanism providing the amount of structural compression required in the region of the distention mechanism to prevent the at least one arm from bowing outwardly in an undesired direction or orientation when the pull wire is retracted by the user, the medical lead being transnasally or transorally insertable in an esophagus of a subject when the distention mechanism is retracted, the method comprising the steps of:

(a) inserting the distal end of the lead transnasally or transorally into the esophagus of the subject, the distention mechanism being in a retracted state;

(b) expanding the distention mechanism in the esophagus so that it assumes an expanded state;

(c) sensing, monitoring or defibrillating a heart of the patient with the medical lead;

(d) retracting the distention mechanism to the retracted state, and (e) removing the lead from the esophagus of the subject.

* * * * *